United States Patent
Zimmerman et al.

(10) Patent No.: US 9,452,059 B2
(45) Date of Patent: Sep. 27, 2016

(54) INTERVERTIBRAL DISC CAP AND METHOD OF USE

(71) Applicants: Christian G. Zimmerman, Boise, ID (US); Larry Holmes, Boise, ID (US)

(72) Inventors: Christian G. Zimmerman, Boise, ID (US); Larry Holmes, Boise, ID (US)

(*) Notice: Subject to any disclaimer, the term of this patent is extended or adjusted under 35 U.S.C. 154(b) by 247 days.

(21) Appl. No.: 14/059,162

(22) Filed: Oct. 21, 2013

(65) Prior Publication Data

US 2014/0114416 A1 Apr. 24, 2014

Related U.S. Application Data

(60) Provisional application No. 61/716,297, filed on Oct. 19, 2012.

(51) Int. Cl.
*A61B 17/70* (2006.01)
*A61F 2/44* (2006.01)
*A61F 2/46* (2006.01)
*A61F 2/30* (2006.01)

(52) U.S. Cl.
CPC ............... *A61F 2/442* (2013.01); *A61F 2/44* (2013.01); *A61F 2/4611* (2013.01); *A61F 2002/30171* (2013.01); *A61F 2002/30245* (2013.01); *A61F 2002/30772* (2013.01); *A61F 2002/30881* (2013.01); *A61F 2002/4435* (2013.01); *A61F 2310/00017* (2013.01); *A61F 2310/00023* (2013.01); *A61F 2310/00029* (2013.01)

(58) Field of Classification Search
CPC .... A61F 2/4455; A61F 2/447; A61F 2/4611; A61F 2002/464; F16B 23/0007; F16B 23/0038; F16B 5/0233

USPC ................................................ 411/403, 410
See application file for complete search history.

(56) References Cited

U.S. PATENT DOCUMENTS

| | | | | |
|---|---|---|---|---|
| 2,931,265 A * | 4/1960 | De Lacy | ............... | F16B 23/00 411/403 |
| 4,936,851 A * | 6/1990 | Fox | ............... | A61B 10/00 623/16.11 |
| 5,055,104 A * | 10/1991 | Ray | ............... | A61B 17/1757 606/247 |
| 5,458,638 A * | 10/1995 | Kuslich | ............... | A61F 2/4455 606/247 |
| 5,683,394 A * | 11/1997 | Rinner | ............... | A61F 2/4455 606/247 |
| 5,762,457 A * | 6/1998 | Lide | ............... | B25B 13/065 411/405 |
| 5,785,710 A * | 7/1998 | Michelson | ............... | A61B 17/1671 606/247 |
| 5,895,427 A * | 4/1999 | Kuslich | ............... | A61F 2/4455 128/898 |
| 6,168,631 B1 * | 1/2001 | Maxwell | ............... | A61B 17/562 623/17.11 |
| 6,290,724 B1 * | 9/2001 | Marino | ............... | A61F 2/4455 623/17.11 |
| 6,758,849 B1 * | 7/2004 | Michelson | ............... | A61F 2/30744 606/247 |
| 8,808,338 B2 * | 8/2014 | Martin | ............... | A61B 17/1717 606/301 |

* cited by examiner

*Primary Examiner* — Anu Ramana
(74) *Attorney, Agent, or Firm* — Robert L. Shaver; Shaver & Swanson, LLP

(57) ABSTRACT

An intervertebral spacer in the form of a generally flat four sided disc, with two opposite sides having slightly curved surfaces and two opposite sides having pointed lobes. The disc is configured to be placed between two vertebrae and rotated, with the rotation spreading the vertebrae and moving the pointed lobes into contact with the inner vertebral faces, for holding the vertebrae a fixed distance apart.

3 Claims, 4 Drawing Sheets

INTERVERTIBRAL DISC CAP AND METHOD OF USE

PRIORITY/CROSS-REFERENCE TO RELATED APPLICATIONS

This application claims the benefit of U.S. Provisional Application No. 61/716,297, filed Oct. 19, 2012 the disclosure of which is incorporated by reference.

TECHNICAL FIELD

The disclosed technology generally relates to tools and methods for spine surgery, and more particularly to spacing devices between vertebrae.

BACKGROUND

The purpose of the Abstract is to enable the public, and especially the scientists, engineers, and practitioners in the art who are not familiar with patent or legal terms or phraseology, to determine quickly from a cursory inspection, the nature and essence of the technical disclosure of the application. The Abstract is neither intended to define the inventive concept(s) of the application, which is measured by the claims, nor is it intended to be limiting as to the scope of the inventive concept(s) in any way.

Background Information

There are 65 million lower back pain sufferers in the United States alone. It is the number one medical procedure in terms of cost expenditure. Surgical treatments for lower back pain are three times the cost of cardiac surgical procedures. Approximately 20% of the population experiences lower back pain each year. Typically, 97% of persons fifty years old and older have Degenerative Joint Disease. There are no drug therapies which address this problem appropriately. However there are 540,000 discectomies per year in the U.S., in which the disc between vertebrae is removed and two vertebrae are fused together.

The problem is that this extremely painful medical condition has a recurrence rate of 8-12% after surgical intervention, and a re-operation rate of 5-10%. This causes a deteriorating spiral of patients' back condition, with the attendant pain and medical cost which further burdens an overtaxed system.

SUMMARY

The device and method herein disclosed address the problem of maintaining separation of adjacent vertebrae after the disc between them has been removed, or to prevent pinching of the nerves passing between the vertebrae. This is important in order to prevent pinching of the nerves that extend from the spinal cord out to the limbs, and which pass between the vertebral discs. The device is called an intervertebral disc cap, hereinafter called a disc cap. The disc cap is a generally flattened disc with four sides. It also has a first side and a second side, and on the first side is a recess for a tool such as Allen wrench or hex tool. Other fitting or tools could also be utilized, such as slot or Phillips drivers, star, or other conventional fittings and interfitting tools. The fitting is provided to allow the disc cap to be turned after it is placed between two vertebrae, with the pointed lobes lock it in place by gripping the bone. Turning the disc cap also spreads the vertebrae apart slightly apart, since the disc cap is narrower between the first and second edges than between the third and fourth edges.

The disc has a first edge and a second edge which are generally curved, and are opposite each other. The curved shape helps them rotate 90 degrees after they are placed between the vertebrae. The disc also has a third and a fourth edge which join the first and second edge, with the third and fourth edges each containing at least one pointed lobe.

In one configuration, the third and the fourth edges each contain two pointed lobes with a notch between the lobes. The purpose of the pointed lobes is to bite into the bone of the vertebrae and to secure the disc cap between the vertebrae. The first side of the disc is generally beveled on all four sides and the second side of the disc is generally flat.

The disc cap can be made of typical materials which are used in surgery for long term residence in the human body. In one configuration of the disc cap, three sizes would be provided, with the small having a diameter of approximately 0.6-0.8 centimeters, the medium having a diameter of approximately 0.8-1.2 centimeters, and the large having a diameter of 1.3-1.5 centimeters.

Disclosed is also a method of stabilizing human vertebrae after a discectomy, involving use of the disc cap described above. The disc cap can also be installed between vertebrae in which the disc has not been removed. In the disclosed method, the disc cap is inserted between vertebrae in a generally vertical (with the plane of the first side parallel with the spinal column) orientation, with the second side toward the vertebrae and the first and second edges parallel with the inner vertebral faces. The disc cap is typically placed near the outside and back of the vertebral column, with the recess for the tool or Allen wrench exposed toward the patient's back. A tool or Allen wrench is placed in the recess or hex socket and is used to turn the disc cap 90 degrees so that the pointed lobes of sides three and four bite into the inner faces of the vertebrae. The tool is then removed, and the disc cap is then left in place, and the surgery is closed. The disc cap provides a spacer so that the space between the vertebrae is maintained, and nerves which extend between the vertebrae are not pinched.

Still other features and advantages of the presently disclosed and claimed inventive concept(s) will become readily apparent to those skilled in this art from the following detailed description describing preferred embodiments of the inventive concept(s), simply by way of illustration of the best mode contemplated by carrying out the inventive concept(s). As will be realized, the inventive concept(s) is capable of modification in various obvious respects all without departing from the inventive concept(s). Accordingly, the drawings and description of the preferred embodiments are to be regarded as illustrative in nature, and not as restrictive in nature.

Figure 1:
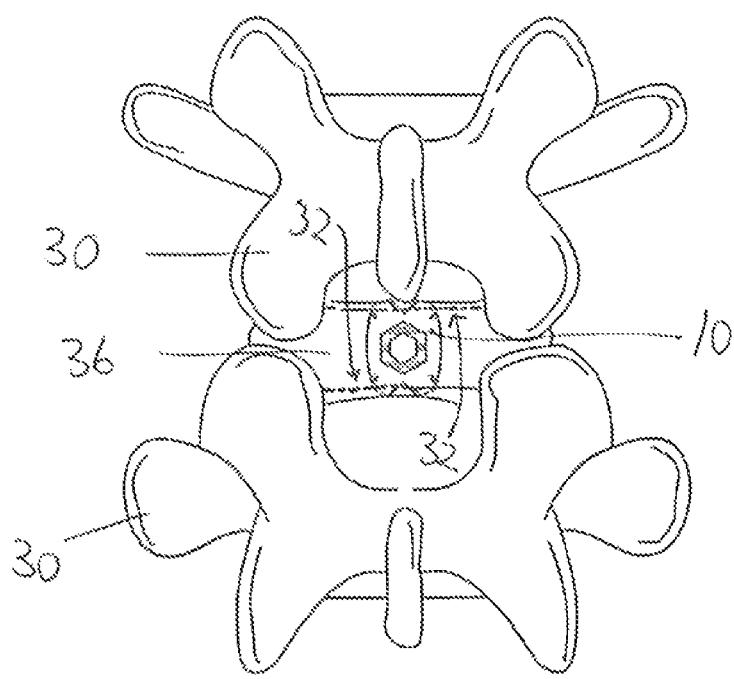
FIG. 1 is an anterior-posterior view of two vertebrae with the disc cap of the disclosed technology between the discs.

DETAILED DESCRIPTION OF THE
EXEMPLARY EMBODIMENTS

While the presently disclosed inventive concept(s) is susceptible of various modifications and alternative constructions, certain illustrated embodiments thereof have been shown in the drawings and will be described below in detail. It should be understood, however, that there is no intention to limit the inventive concept(s) to the specific form disclosed, but, on the contrary, the presently disclosed and claimed inventive concept(s) is to cover all modifications, alternative constructions, and equivalents falling within the spirit and scope of the inventive concept(s) as defined in the claims.

Figure 2:
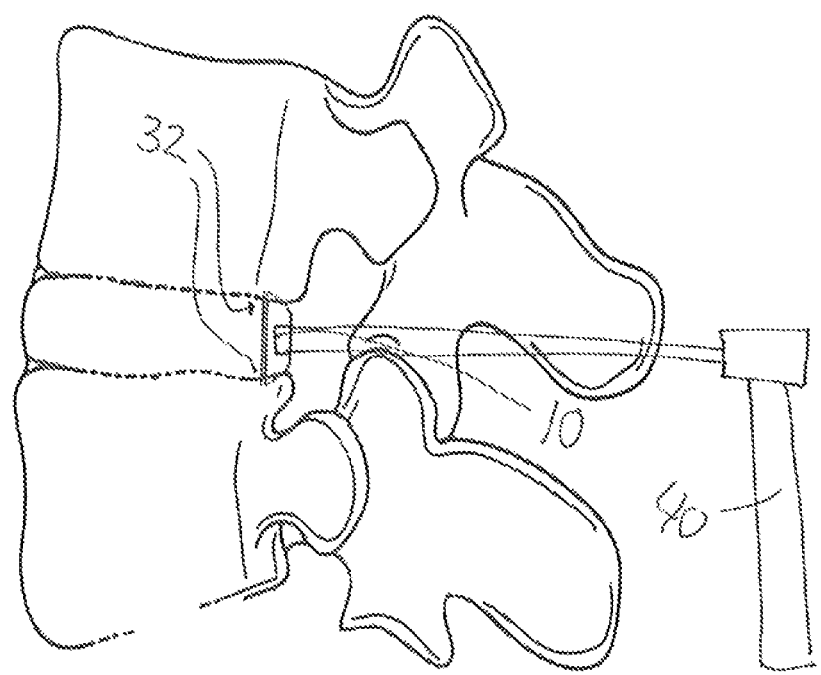
FIG. 2 is a lateral view of two vertebrae with the disc cap of the disclosed technology between them.

A preferred embodiment of the disclosed technology is shown in FIGS. 1 through 6. FIG. 1 shows a disc cap 10 of the present invention inserted between two vertebrae 30. This view is an interior-posterior view. Also shown is the vertebral disc 36 of the patient. The disc cap 10 is inserted between the interfaces 32 of the two vertebrae and maintains a spacing between the two interfaces of the vertebrae, to prevent pinching of nerves which come out of the spinal cord between the vertebrae. Shown in FIG. 2 is a lateral or side view of the disc cap of the disclosed technology in its position between the interfaces 32 of a patient. In FIG. 2 is a tool 40 which is used to turn the disc cap 10.

Figure 3:
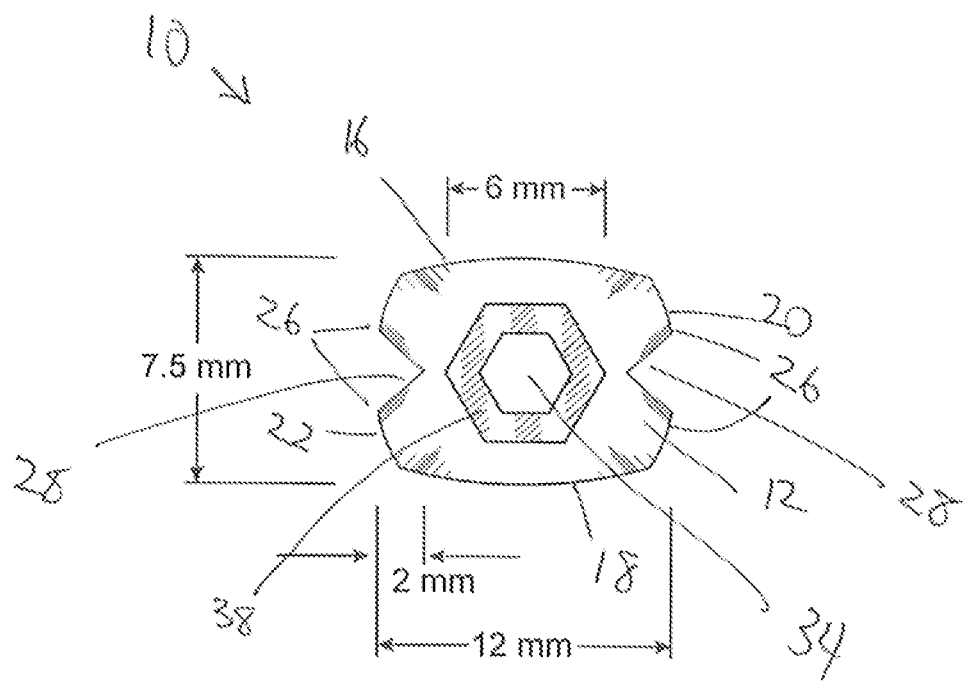
FIG. 3 is a top view of the disc cap of the disclosed technology shown dimensions.
Figure 4:
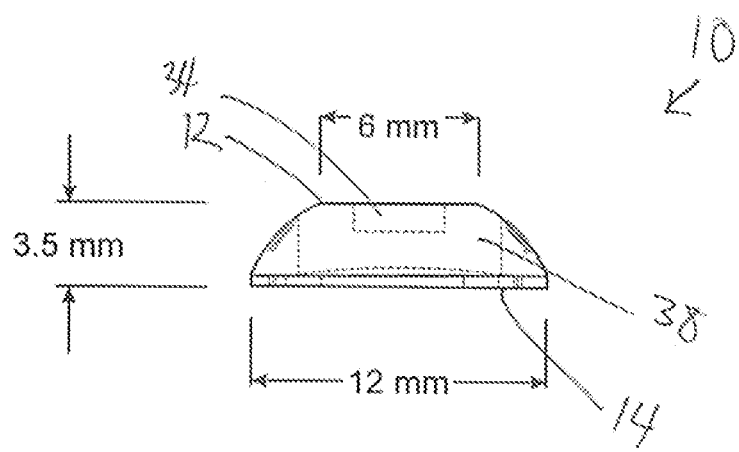
FIG. 4 is a side view of the disclosed technology.

FIG. 3 is a top view of the disc cap 10 of the invention. Shown in FIG. 2 is the front side 12 which has a first edge 16, a second edge 18, a third edge 20 and a fourth edge 22. On the third and fourth edges are pointed lobes 26 separated by a notch 28. Present on the front side 12 is a hex socket 34 which is configured to fit with a hexagonal wrench or wrench tip. Other shapes of tool interfaces are also possible. Shown in FIG. 3 is an insert 38 which surrounds the hex socket 34. The disc cap may be designed with or without the insert 38. The insert 38 is preferably a titanium alloy, but other materials commonly used for long term residence in the human body are also suitable. This can include various alloys of titanium and stainless steel. A preferred titanium alloy includes Vanadium and Cobalt, but materials or alloys which are resistant to corrosion and which are stable in the body for long term residence are suitable. FIG. 4 is another view of the disc cap 10 of the disclosed technology showing the hex socket 34, the insert 38, the front side 12 and the back side 14 of the disc cap.

Figure 5:
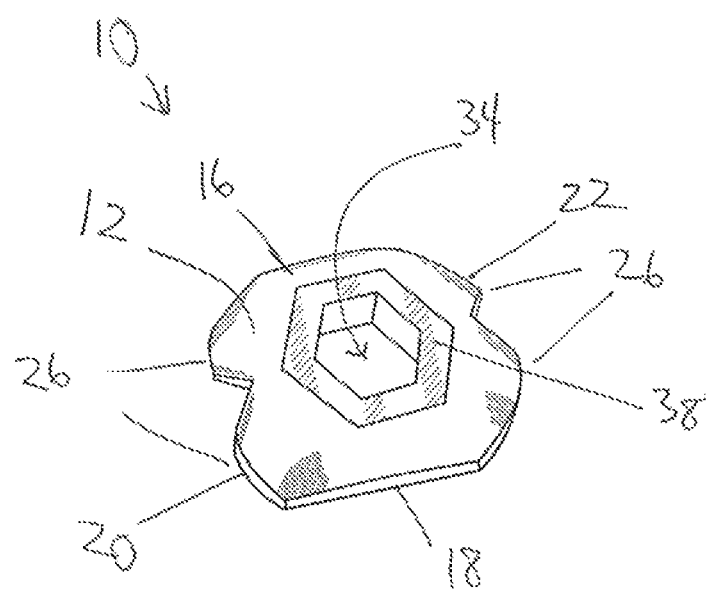
FIG. 5 is a perspective view of the disc cap of the disclosed technology.

FIG. 5 shows a perspective view of the disc cap 10, with the insert 38, the hex socket 34, and the pointed lobes 26.

The dimensions of the device are such that the distance from the first edge 16 and the second edge 18 is a shorter distance than the distance between the tips of the pointed lobes 26 on the third edge 20 and the fourth edge 22. The slightly curved sides 16 and 18 have a curved shape to them and the curve has a function in the use of this device. In use the device is placed with the first edge 16 and the second edge 18 between two vertebrae 30, on the inner face 32 of the vertebrae. The pointed lobes 26 of the disclosed disc cap provide sufficient grip against slipping, but do not tear the dura on the inner face 32 of the vertebrae. Once installed on the vertebrae, the disc cap of the disclosed invention is designed to be left there permanently. Two or more disc caps may be placed between two vertebrae and left there permanently. Other shapes of the disc cap are also possible, such as a shape with teeth on the rim that grip the bone and resist slipping. However, sharp edges are to be avoided so that the dura is not torn.

Figure 6:
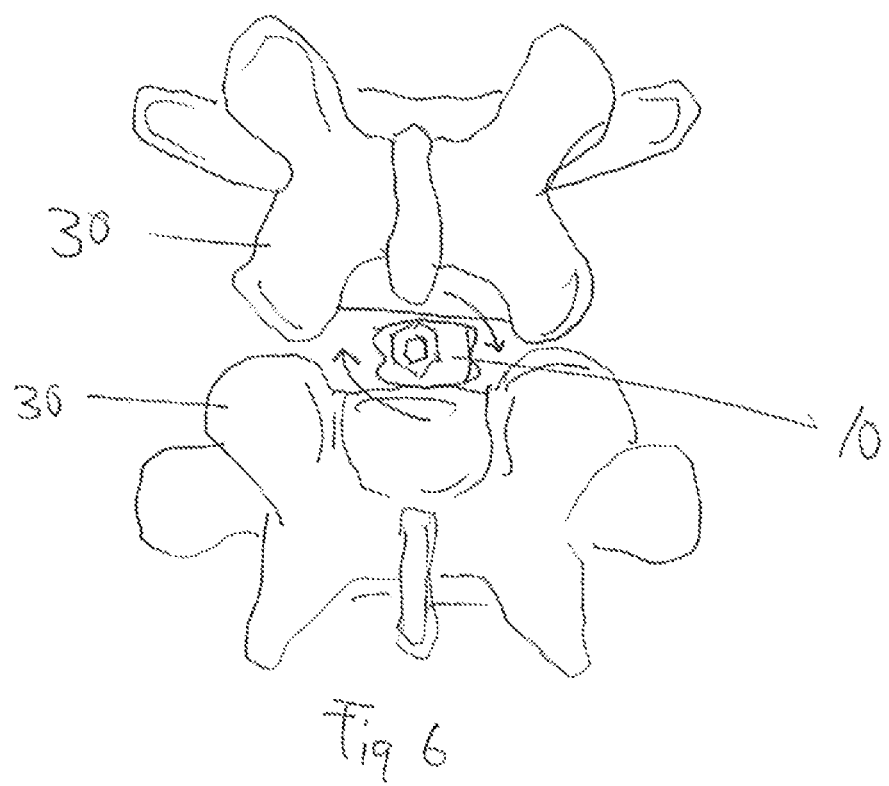
FIG. 6 is an anterior posterior view of the disclosed technology before rotation of the disc.

The disclosed technology is also a method of stabilizing the space between two vertebrae. The method involves the following steps. (1) The disc between two vertebrae is removed. This step is optional because the disc caps of the disclosed technology can be inserted between two vertebrae in which the vertebral disc is not removed. (2) The next step is to insert the disc cap on the inter-vertebral spaces between adjacent vertebrae, with the first edge 16 and the second edge 18 touching the vertebral spaces. The disc cap inserted thusly is shown in FIG. 6.

The next step is to insert a pressure sensitive Allen wrench into the hex socket 34 of the disclosed device. This is shown in FIG. 2. Once the Allen wrench is inserted into the hex socket 34, a rotating force is applied to the hex socket which causes the disc cap to rotate so that the pointed lobes 26 roll into contact with the first edge 16 and the second edge 18. The rotation of the disc cap is indicated in FIG. 6. The tool 40 is shown in FIG. 2. The pressure sensitive wrench for use in the hex socket is a sensitive torque wrench with a preferred torque being set at approximately 50 inch lbs. The disc cap is rotated 90 degrees until the pointed lobes contact the inner vertebral faces, as shown in FIG. 1.

The next step is to remove the Allen wrench and close up the operating site, leaving the disc cap in place in the patients spine for an indefinite period.

While certain exemplary embodiments are shown in the Figures and described in this disclosure, it is to be distinctly understood that the presently disclosed inventive concept(s) is not limited thereto but may be variously embodied to practice within the scope of the following claims. From the foregoing description, it will be apparent that various changes may be made without departing from the spirit and scope of the disclosure as defined by the following claims.

What is claimed is:

1. A method of vertebral stabilization, comprising the steps of:
    placing a generally flattened four sided disc between two human vertebrae, said flattened disc comprising a generally flat second side, and a first side with 4 tapering sides forming four disc edges, and with said second side being beveled along said edges, with a first and second opposing edges having straight slightly curved edges generally opposite each other, with the third and fourth edges each having a pair of pointed lobes with a notch between said lobes, with said second side having a recess for a tool, with said disc placed on edge between two vertebrae with said slightly curved edges on vertebrae inner faces and with said tool recess accessible from outside said vertebrae;
    inserting a tool into said tool recess;
    turning said tool and said flattened disc ninety degrees using said tool until said sides with said pointed lobes on said third and fourth edges contact said vertebrae faces;
    removing said tool from contact with said disc; and
    leaving said disc between said adjacent vertebrae as a spacer to prevent contact between said adjacent vertebral faces with nerves between said adjacent vertebrae.

2. The method of claim 1, in which said tool recess is a socket having a polygonal cross-section for receiving a tool having multiple flat faces.

3. The method of claim 1 in which said tool has a maximum torque setting.

* * * * *